US00PP20245P2

(12) United States Plant Patent

Hanes

(10) Patent No.: US PP20,245 P2

(45) Date of Patent: Sep. 1, 2009

(54) *PELARGONIUM* PLANT NAMED 'AMRI TRARED'

(50) Latin Name: *Pelargonium interspecific*
Varietal Denomination: Amri Trared

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/218,433

(22) Filed: Jul. 15, 2008

(51) Int. Cl.
*A01H 5/00* (2006.01)

(52) U.S. Cl. ..... Plt./324; Plt./330

(58) Field of Classification Search ..... Plt./324, Plt./330
See application file for complete search history.

*Primary Examiner*—Kent L Bell
(74) *Attorney, Agent, or Firm*—S. Matthew Edwards

(57) ABSTRACT

A new *Pelargonium* plant named 'Amri Trared', particularly distinguished by the dark red flower color, large flower size, novel lateral plant habit, zonal like branching and foliage, and good garden performance growing well in both sun and semi-shade.

1 Drawing Sheet

Latin name of the genus and species of the plant claimed: *Pelargonium interspecific.*

Varietal denomination: 'Amri Trared'.

BACKGROUND OF THE NEW PLANT

The present invention comprises a new *Pelargonium*, botanically known as *Pelargonium interspecific*, and hereinafter referred to by the variety name 'Amri Trared'.

'Amri Trared' is a product of a planned breeding program. The new cultivar 'Amri Trared' has a novel, lateral plant habit, zonal like branching and foliage, novel dark red flower color, good garden performance growing well in both sun and slight shade, and large flower size.

'Amri Trared' originated from an interspecific hybridization in a controlled breeding program in Gilroy, Calif. U.S.A. The female parent was an *hortorum* hybrid seedling identified as '10136-1', not patented. '10136-1' has a lighter red color, more upright plant habit, and a smaller flower than 'Amri Trared'.

The male parent of 'Amri Trared' was an unpatented interspecific hybrid seedling identified as '9876-3', a red color. '9876-3 has smaller, single flowers, and lighter green foliage than 'Amri Trared'.

'Amri Trared' was selected as one flowering plant within the progeny of the stated cross in November 2005 in a controlled environment in Gilroy, Calif., U.S.A.

The first act of asexual reproduction of 'Amri Trared' was accomplished when vegetative cuttings were used from the initial selection in the November 2005 in a controlled environment in Gilroy, Calif., U.S.A.

Horticultural examination of plants grown from cuttings of the plant initiated in January 2006 in Gilroy, Calif., U.S.A. and continuing thereafter, has demonstrated that the combination of characteristics as herein disclosed for 'Amri Trared' are firmly fixed and are retained through successive generations of asexual reproduction.

'Amri Trared' has not been observed under all possible environmental conditions. The phenotype may vary significantly with variations in environment such as temperature, light intensity, and day length.

Plant Breeder's Rights for this cultivar were applied for in Canada on Aug. 23, 2007 and in Germany on Jul. 2, 2007. A United States provisional application was applied for on Nov. 15, 2007 and assigned U.S. Ser. No. 60/988,364. The title of the application was "Flower Pigmentation in Pelargonium Hortorum." 'Amri Trared' has not been made publicly available more than one year prior to the filing of this application.

BRIEF DESCRIPTION OF THE NEW VARIETY

The accompanying photographic drawing shows typical flower and foliage characteristics of 'Amri Trared' with colors being as true as possible with an illustration of this type. The photographic drawings show a flowering potted plant of the new variety, and a close-up of the flowers/umbel.

DETAILED BOTANICAL DESCRIPTION

The measurements were taken in Gilroy, Calif. U.S.A., in August 2007 on plants that were growing in a 16 inch container containing 3 plants each. Cultures of these plants started in the greenhouse in April 2007 and were transferred to the outdoor containers in early June 2007.

Color Chart used: Royal Horticultural Society Colour Chart (R.H.S.) 2001.

BRIEF SUMMARY OF INVENTION

The following observations, measurements, and comparisons describe plants grown outside in Gilroy, Calif., U.S.A. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Amri Trared' | 'Americana Dark Red' (U.S. Plant Pat. No. 9,307) |
|---|---|---|
| Flower color/size | Darker red/larger | Little lighter red/smaller |
| Plant habit | Upright and lateral | Upright |
| Foliage size | Larger leaf | Smaller leaf |

Plant:

*Form, growth and habit.*—Upright, outwardly spreading and rounded growth habit. Vigorous, well branched and grows well in sun or semi-shade.

*Plant height.*—12–14 cm.

*Plant height* (*inflorescence included*).—20–24 cm.

*Plant width.*—14–18 cm.

Foliage:

*Arrangement.*—Alternate, simple.

*Immature, leaf color, upper surface.*—Between RHS 144A and 144B. Lower surface: Between RHS 146B and 146C.

*Mature, leaf color, upper surface.*—Closest to RHS 146A. Lower surface: Between RHS 146B and 146C.

*Length.*—4.3–4.6 cm.

*Width.*—8–8.4 cm.

*Shape.*—Orbicular.

*Base shape.*—Cordate.

*Apex shape.*—Rounded.

*Margin.*—Deeply lobed; irregularly crenate.

*Texture.*—Hirsute, glandular hairs.

*Color of zone.*—Very subtle hue of RHS 187A.

*Zonation diameter.*—Approximately 1.5 cm.

*Color of veins, upper surface.*—Indistinct.

*Color of veins, lower surface.*—Slight hue of RHS 144A.

*Petioles color.*—RHS 144A.

*Petioles length.*—3.5–4 cm.

*Diameter of petiole.*—0.2–0.3 cm.

*Texture.*—Hirsute; long glandular hairs.

Stem:

*Color of stem.*—Closest to RHS 144A.

*Length of stem.*—8–10 cm.

*Diameter.*—0.9–1.3 cm.

*Length of internodes.*—1–2 cm.

*Texture.*—Hirsute; some glandular hairs.

Inflorescence:

*Type.*—An umbel.

*Number of flowers and buds per inflorescence.*—12–20.

*Umbel persistence on plant.*—Approximately 14 days.

*Umbel diameter.*—10–13 cm.

*Umbel depth.*—6.5–7 cm.

*Color of peduncle.*—RHS 144A, with anthocyanin blotches of R.H.S. 183.

*Length of peduncle.*—13–16 cm.

*Peduncle diameter.*—0.3–0.4 cm.

*Texture.*—Villous; glandular hairs.

*Pedicel color.*—RHS 183C.

*Length of pedicel.*—2.7–3.3 cm.

*Diameter of pedicel.*—0.1–0.15 cm.

*Texture.*—Hirsute; glandular hairs of various sizes.

Corolla:

*Form.*—Polypetalous, overlapping.

*Number of petals.*—6–8.

*Width of flower.*—5.3–5.6 cm.

*Color upper and lower petals, Upper surface.*—Closest to RHS 46B, but more velvety and bluish-red; RHS 155B basally, but whiter; subdued hue of RHS 187A veins.

*Color upper and lower petals, Lower surface.*—Closest to RHS 45B, but more blueish-red.

*Length of upper and lower petals.*—2.6–2.7 cm.

*Width of upper and lower petals.*—1.8–1.9 cm.

*Petal shape.*—Obovate.

*Apex shape.*—Rounded.

*Margin.*—Entire.

*Petal texture.*—Papillose.

*Number of petaloids.*—None.

*Duration of flowering.*—Continuous flowering throughout the Summer.

Bud (just before opening):

*Color.*—RHS 46A.

*Length.*—1.2–1.7 cm.

*Width.*—0.6–1.0 cm.

*Shape.*—Narrowly elliptical to lanceolate.

*Number of sepals.*—5, fused at base.

*Color of sepals.*—RHS 144A heavily covered with anthocyanin blotches of RHS 183A.

*Length of sepals.*—1.0–1.1 cm.

*Width of sepals.*—0.2–0.3 cm.

*Sepal shape.*—Lanceolate.

*Apex shape.*—Acute.

*Margins.*—Entire.

*Texture.*—Villous; hirsute; glandular hairs.

Reproductive organs:

*Pistil.*—1.

*Length.*—0.8–0.9 cm.

*Style color.*—RHS 46A.

*Style length.*—0.2–0.3 cm.

*Stigma color.*—RHS 46A.

*Number of anthers.*—8–10.

*Length filaments.*—0.5–0.7 cm.

*Color of filaments.*—RHS 155C.

*Pollen amount.*—Moderate.

*Color of pollen.*—RHS N163A.

Fertility/seed set: Not observed on this hybrid.

Disease/pest resistance: Disease resistance and/or susceptibility has not been observed on this hybrid.

What is claimed is:

1. A new and distinct variety of *Pelargonium* plant named 'Amri Trared,' substantially as illustrated and described herein.

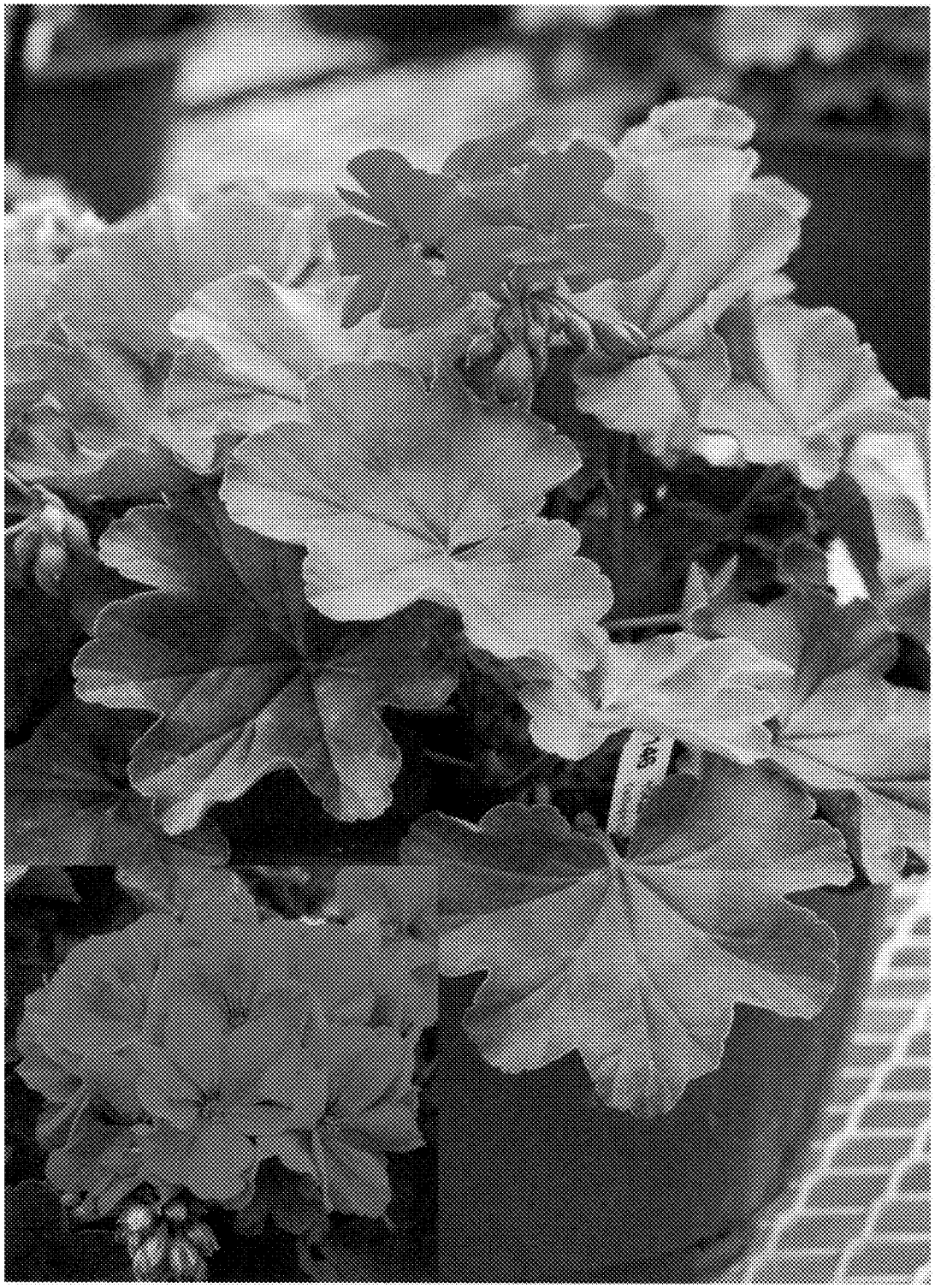

* * * * *